United States Patent [19]

McGredy, IV

[11] Patent Number: Plant 5,519

[45] Date of Patent: Jul. 23, 1985

[54] HYBRID TEA ROSE PLANT VC. MACAUCK

[75] Inventor: Samuel McGredy, IV, Auckland, New Zealand

[73] Assignee: Armstrong Nurseries, Inc., Ontario, Calif.

[21] Appl. No.: 556,544

[22] Filed: Nov. 30, 1983

[51] Int. Cl.[3] ..... A01H 5/00

[52] U.S. Cl. ..... Plt./20

[58] Field of Search ..... Plt./20

*Primary Examiner*—Robert E. Bagwill

*Attorney, Agent, or Firm*—Synnestvedt & Lechner

[57] ABSTRACT

A new hybrid red tea rose for cut flowers and garden decoration, having as its seed parent Red Planet and as its pollen parent Pharoah, Plant Pat. No. 2825. The new cultivar produces nearly continual, abundant, brilliant and lasting long-stemmed red flowers with a heavy petal substance lending to their longer-than-average longevity, both in the garden and in the vase. The cultivar exhibits consistent vigor and bloom performance under a wide range of climatic conditions and has above-average disease resistance under Ontario, California, growing conditions.

1 Drawing Figure

This invention relates to a new class of Hybrid Tea Rose cv. Macauck. The plant is a hardy, outdoor seedling of the medium-height bush type, cultivated for cut flowers and garden decoration. It was propagated by Samuel McGredy IV in Auckland, New Zealand, having as its seed parent Red Planet and as its pollen parent Pharaoh, U.S. Plant Pat. No. 2,825.

The new rose plant cv. Macauck is particularly characterized by the following combination of characteristics: the brilliant, lasting red coloration of its flowers, essentially as described and illustrated; its heavy petal substance that lends to longer-than-average flower longevity both in the garden and in the vase; its consistent vigor and bloom performance under a wide range of climatic conditions; its above-average disease resistance under Ontario, Calif., growing conditions; and its abundant and nearly continual production of long-stemmed flowers. It holds these distinguishing characteristics through succeeding propagations by budding.

This new rose may be distinguished from its seed parent, Red Planet, by the following combination of characteristics: Red Planet bears blossoms of $3\frac{1}{2}$ to $4\frac{1}{2}$ inch diameter under Ontario, Calif. growing conditions, whereas the new seedling produces significantly larger blooms, of $4\frac{1}{2}$ to $5\frac{1}{2}$ inch diameter, essentially as described and illustrated herein, under similar growing conditions. The bush of Red Planet has foliage with a glossy finish, whereas the new seedling's foliage has a more dull, semi-glossy finish.

The new cultivar rose Macauck may be distinguished from its pollen parent, Pharaoh (U.S. Plant Pat. No. 2,825), by the following combination of characteristics: Pharaoh bears flowers of $5\frac{1}{2}$ to 6-inch diameter under Ontario, Calif., growing conditions, whereas the new rose bears significantly smaller blooms, of $4\frac{1}{2}$ to $5\frac{1}{2}$ inch diameter, essentially as described and illustrated herein. Whereas the new rose usually bears medium-sized, pointed and ovoid buds, Pharaoh bears significantly larger, more globular buds. The new rose produces a bush with medium-sized, semi-glossy foliage, whereas Pharaoh produces a bush with significantly larger, glossy foliage.

FLOWER

The new variety usually bears its flowers singly, sometimes 3 to 4 flowers per stem in irregular clusters, on strong stems that are long for the class. Outdoors, the plant blooms nearly continuously and in very abundant quantities during the growing season. It has a slight to moderate tea fragrance.

The accompanying drawing illustrates the plant in color and shows the flowering thereof from bud to full bloom.

Throughout its specification, color names beginning with a small letter signify that the name of that color as used in common speech is aptly descriptive. Color names beginning with a capital letter designate values based upon The R.H.S. Colour Chart of The Royal Horticultural Society in London, England.

BUD

The peduncle is of short to average length for the class and of average to heavy caliper, strong, erect, and stiff. It is moderately smooth with some stipitate glands and between Yellow-Green 146C and Green 138B in coloration.

Before the calyx breaks, the bud is medium in size for the class and of medium length, pointed and ovoid in form, with few stipitate glands on the surface of the bud. There are usually slender foliaceous parts extending beyond the tip of the bud equal to one-half or more of its length.

As the calyx breaks, the bud color is between Red 53A and Greyed-Purple 187A.

The inner surface of the sepals has a fine, woolly tomentum; margins are lined with stipitate glands.

As the first petal opens, the bud is average in size for the class, of medium length and pointed-ovoid in form. The color on the outside and inside is between Red 53A and Red 46A. The bud opens up well and is not prevented from opening by cold, hot, wet, or dry weather.

BLOOM

The size of the bloom when fully open is average to large for the class, ranging from $4\frac{1}{2}$ to $5\frac{1}{2}$ inches in diameter. The petalage is double, with from 32 to 37 petals and from 1 to 5 petaloids; the petals are arranged regularly. The bloom form when half open is moderately high-centered. The petals are spiraled, with the petal edges somewhat reflexed outward. When fully open, the bloom is moderately cupped, with petals similarly cupped. Petal edges are somewhat reflexed outward.

The petals are of moderately heavy substance and of thick texture, with the insides velvety and the outsides shiny to satiny. The outside petals are nearly round to broadly ovate, with a rounded apex. The intermediate petals are nearly round to broadly ovate, with a rounded apex. The inside petals are broadly ovate and have a rounded apex. The colors may be modified by being shaded or washed or tinted with other colors.

The paragraph immediately following describes the color values observed in a flower newly opened in the month of May. The plant described had been grown outdoors in Ontario, Calif.

The outside surface of the outside, intermediate, and inner petals has a color between Red 53A and Red 45C. The inside surface of the outside, intermediate, and inner petals has a color between Red 46A and Red 45C.

The paragraph immediately following describes color values observed in a bloom which had been open for three days in the month of May. The plant described had been grown outdoors in Ontario, Calif.

The outside surface of the outside and inside petals has a color between Red-Purple 60A and Red 53B. The inside surface of the outside and inside petals has a color between Red 53B and Red 46C.

The general color effect of the newly opened flower is between Red 46A and Red 45C. After being open three days, the bloom gives a general color effect which is between Red 53B and Red 46C. The petals drop off cleanly and are not particularly affected by cold, hot, wet, or dry weather.

In May, roses grown in the garden last on the bush from 4 to 5 days; cut roses grown outdoors and kept at living-room temperatures will last from 6 to 7 days.

REPRODUCTIVE ORGANS

Many stamens are arranged regularly about the pistils and a few are mixed with petaloids.

The filaments are of a medium to long length. Most are with anthers.

The anthers are of medium to large size, and all open approximately at once. Their color when immature is near Yellow 13B and when mature, near Greyed-Orange 166A.

Pollen is abundant in quantity and near Yellow-Orange 18C in color.

There are an average number of pistils (approximately 65).

The styles are uneven, average to long in length, of thin to average caliper, and loosely bunched.

Most ovaries are enclosed in the calyx.

The stigma is near Yellow 4C in color.

The hips are of average length and ovoid to globular in shape. Their color when immature is near Yellow-Green 146B, and they have moderately smooth, thick, and fleshy walls.

Sepals fall soon.

Seeds are average to many in number (12–20) and are of medium size.

FOLIAGE

The compound leaves are borne abundantly and usually comprise from 3 to 5 leaflets. The leaves are of medium size for the class, moderately heavy, and semi-glossy. The leaflets are oval in shape and have an acute apex and a round to acute base. The margin is irregularly serrate.

The mature foliage displays upon its upper surface a color which is between Yellow-Green 147A and Green 139A. The under surface is near Yellow-Green 147B and Yellow-Green 148B.

The upper surface of the young foliage is between Green 137B and Yellow-Green 146B in color and washed lightly with near Greyed-Purple 183C. Its under surface is between Green 139C and Yellow-Green 148C in color and washed with near Greyed-Purple 183C.

The rachis is of average to heavy size, grooved on its upper side, with a few stipitate glands on the edges. The underside is sparsely prickly.

The stipules are of medium length, moderately narrow with medium-length points, turning out at an angle of usually less than 45 degrees.

The plant displays a more-than-average resistance to mildew, rust, and blackspot compared to other commercial varieties grown under comparable conditions in Ontario, Calif.

GROWTH

The plant is bushy, of medium height and upright habit, and is much branched. It displays very vigorous growth. The canes are of medium to heavy caliper for the class.

The main stems are between Yellow-Green 146C and Yellow-Green 147A in color. They bear several large prickles which are of short to medium length for the class. They are almost straight, hooked slightly downward, and have broad base of short to medium length. Prickle color is between Greyed-Orange 166B and Greyed-Orange 166C. There are a very few small prickles of between Greyed-Orange 166B and Greyed-Orange 166C coloration. There are no hairs.

The branches are of a color between Yellow-Green 146B and Green 139B. They bear several large prickles which are of medium length for the class. The large prickles are almost straight, hooked slightly downward, and have broad base of medium length and a color between Greyed-Yellow 162B and Greyed-Yellow 160C. The branches have a few small prickles of the same color as the large prickles. There are no hairs.

New shoots are between Yellow-Green 144A and Green 138B in color. They bear several large prickles which are of medium length for the class, almost straight, hooked slightly downward, and which have a medium-length, broad base. The large prickles are near Greyed-Yellow 160C in color. There are several small prickles, of the same color as the large prickles, and no hairs.

I claim:

1. A new and distinct variety of rose plant of the hybrid tea class, substantially as herein shown and described, being particularly characterized by the brilliant, lasting red coloration of its flowers, essentially as described and illustrated; its heavy petal substance that lends to longer-than-average flower longevity both in the garden and in the vase; its consistent vigor and bloom performance under a wide range of climatic conditions; its above-average disease resistance; and its abundant and nearly continual production of long-stemmed flowers.

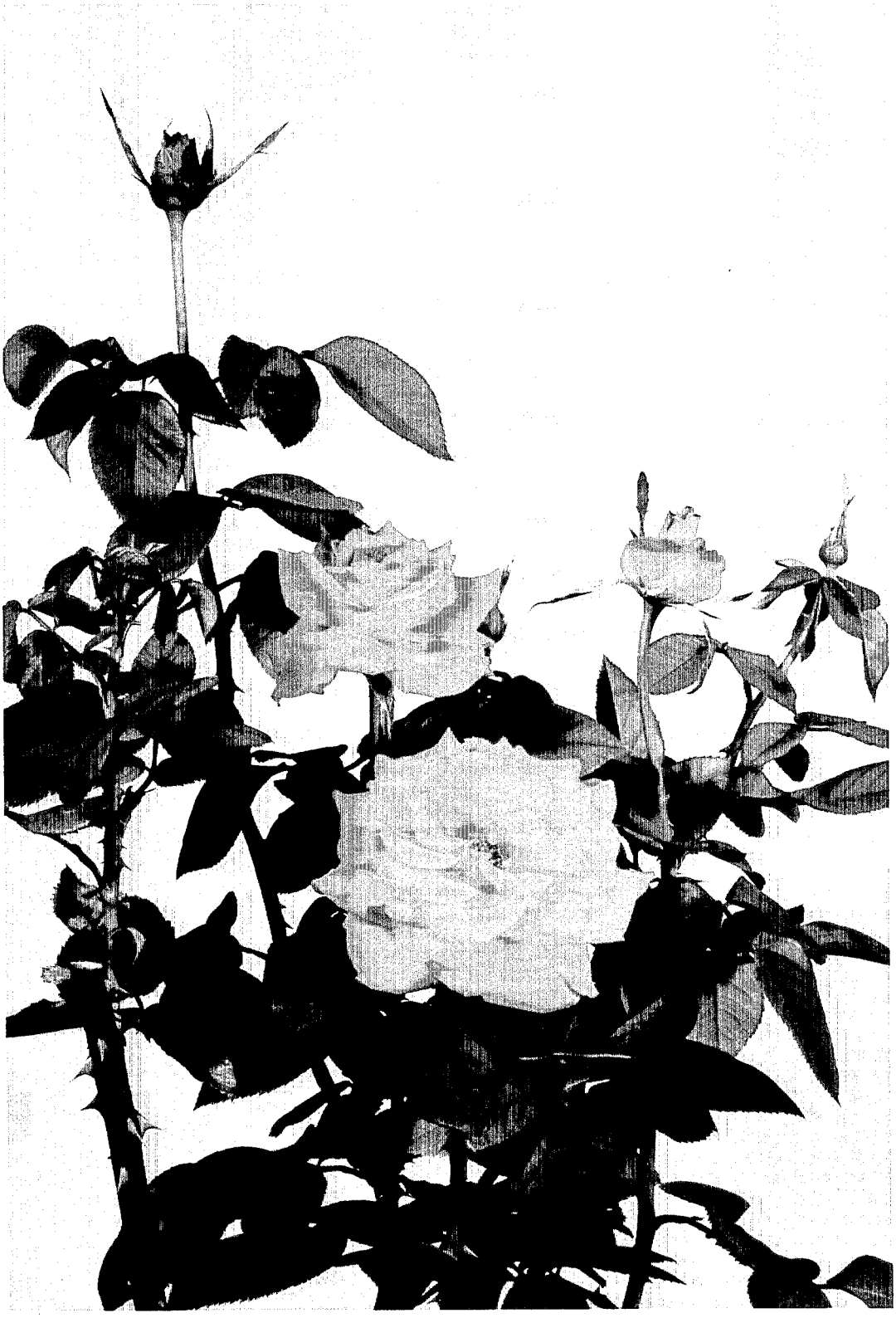

* * * * *